United States Patent
Toth et al.

(10) Patent No.: US 6,993,117 B2
(45) Date of Patent: *Jan. 31, 2006

(54) METHOD AND APPARATUS OF MODULATING THE FILTERING OF RADIATION DURING RADIOGRAPHIC IMAGING

(75) Inventors: Thomas L. Toth, Brookefield, WI (US); Tsur Bernstein, Glendale, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/935,292

(22) Filed: Sep. 7, 2004

(65) Prior Publication Data

US 2005/0031084 A1    Feb. 10, 2005

Related U.S. Application Data

(63) Continuation of application No. 10/064,172, filed on Jun. 18, 2002, now Pat. No. 6,836,535, which is a continuation-in-part of application No. 10/063,420, filed on Apr. 22, 2002.

(51) Int. Cl.
*G21K 3/00*        (2006.01)

(52) U.S. Cl. ....................................... 378/156; 378/157
(58) Field of Classification Search ........ 378/156–160, 378/16

See application file for complete search history.

(56) References Cited

U.S. PATENT DOCUMENTS

| | | | | |
|---|---|---|---|---|
| 5,185,775 A | * | 2/1993 | Sirvin ......................... | 378/156 |
| 5,483,572 A | * | 1/1996 | Hoornaert et al. .......... | 378/156 |
| 6,148,062 A | * | 11/2000 | Romeas ...................... | 378/156 |
| 6,764,217 B2 | * | 7/2004 | Yasuda et al. ............... | 378/205 |
| 2002/0186817 A1 | * | 12/2002 | Schukalski et al. ......... | 378/156 |

FOREIGN PATENT DOCUMENTS

JP        353068994 A  *  6/1978

* cited by examiner

*Primary Examiner*—David V. Bruce
*Assistant Examiner*—Hoon Song
(74) *Attorney, Agent, or Firm*—Ziolkowski Patent Solutions Group, SC; Michael A. Della Penna; Carl B. Horton

(57) ABSTRACT

The present invention includes a filtering apparatus for a CT imaging system or equivalently for an x-ray imaging system. The filtering apparatus may be translated along a first axis or a transverse axis to with respect to an attenuation pattern of a subject during an imaging session to reduce radiation exposure to anatomical regions of the subject sensitive to radiation exposure and/or regions from which data is not being acquired.

5 Claims, 6 Drawing Sheets

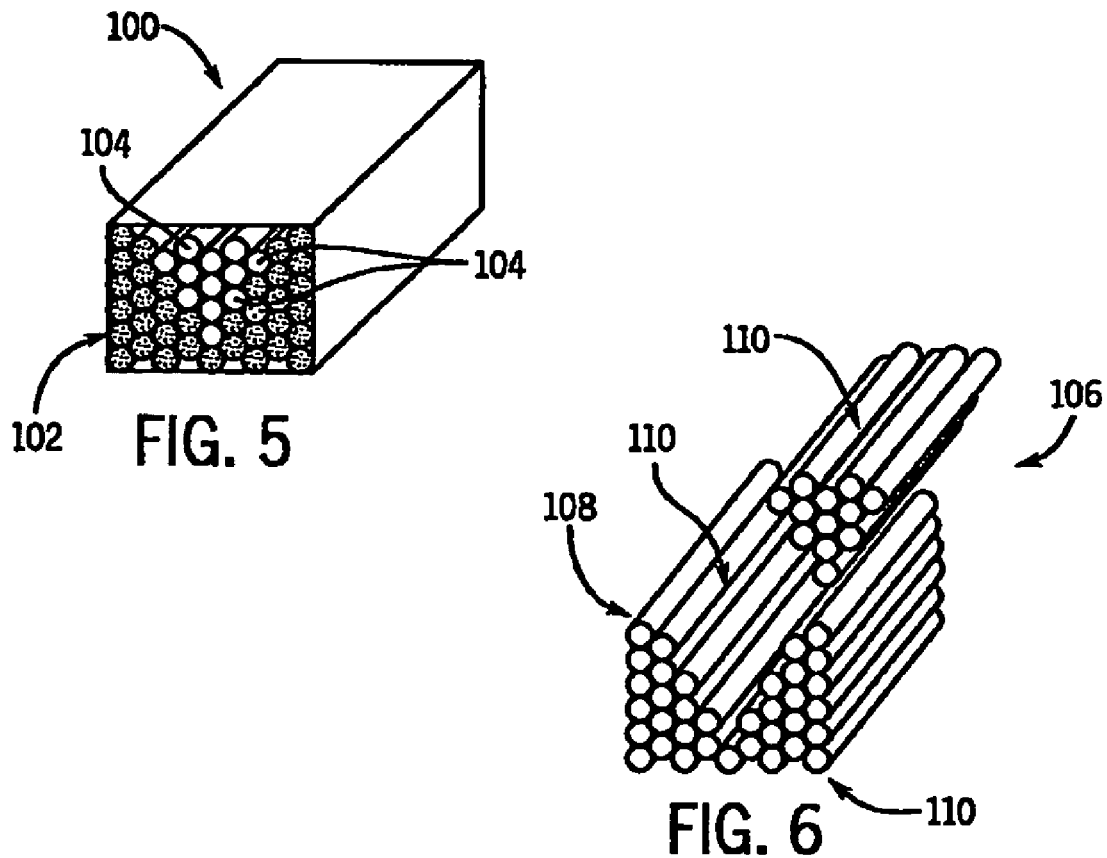
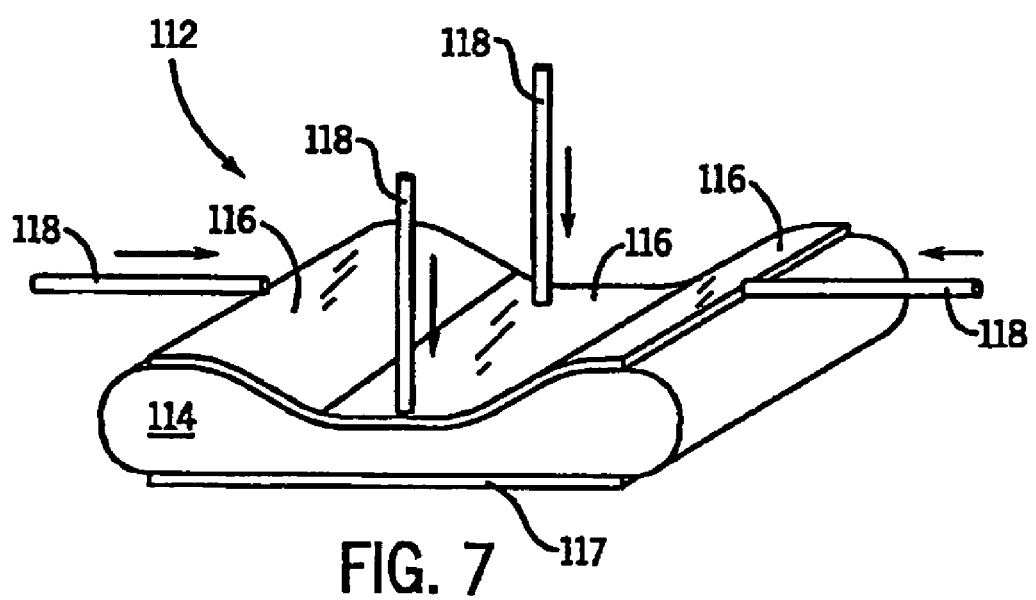

METHOD AND APPARATUS OF MODULATING THE FILTERING OF RADIATION DURING RADIOGRAPHIC IMAGING

CROSS REFERENCE TO RELATED APPLICATIONS

The present application is a continuation of U.S. patent application Ser. No. 10/064,172 filed Jun. 18, 2002, now U.S. Pat. No. 6,836,535 which is a continuation-in-part of U.S. patent application Ser. No. 10/063,420 filed Apr. 22, 2002, both of which are incorporated herein by reference.

BACKGROUND OF THE INVENTION

The present invention relates generally to diagnostic imaging and, more particularly, to a method and apparatus of dynamically filtering radiation emitted toward a subject during radiographic imaging.

Typically, in radiographic imaging systems, an x-ray source emits x-rays toward a subject or object, such as a patient or a piece of luggage. Hereinafter, the terms "subject" and "object" may be interchangeably used to describe anything capable of being imaged. The beam, after being attenuated by the subject, impinges upon an array of radiation detectors. The intensity of the attenuated beam radiation received at the detector array is typically dependent upon the attenuation of the x-rays. Each detector element of the detector array produces a separate electrical signal indicative of the attenuated beam received by each detector element. The electrical signals are transmitted to a data processing system for analysis which ultimately produces an image.

In computed tomography (CT) imaging systems, the x-ray source and the detector array are rotated about a gantry within an imaging plane and around the subject. X-ray sources typically include x-ray tubes, which emit the x-rays as a beam at a focal point. X-ray detectors typically include a collimator for collimating x-ray beams received at the detector, a scintillator for converting x-rays to light energy adjacent the collimator, and a photodiode for receiving the light energy from an adjacent scintillator and producing electrical signals therefrom. Typically, each scintillator of a scintillator array converts x-rays to light energy. Each photodiode detects the light energy and generates a corresponding electrical signal. The outputs of the photodiodes are then transmitted to the data processing system for image reconstruction.

There is increasingly a need to reduce radiation dosage projected toward a patient during an imaging session. It is generally well known that significant dose reduction may be achieved by using a "bowtie" filter to shape the intensity profile of an x-ray beam. Surface dose reductions may be as much as 50% using a bowtie filter. It is also generally known that different anatomical regions of a patient may advantageously mandate different shaped bowtie filters to reduce radiation dosage. For example, scanning of the head or small region of a patient may require a bowtie filter shaped differently than a filter used during a large body scanning session. It is therefore desirable to have an imaging system with a large number of bowtie filter shapes available to best fit each patient. However, fashioning an imaging system with a sufficient number of bowtie filters to accommodate the idiosyncrasies encountered during scanning of numerous patients can be problematic in that each individual patient cannot be contemplated. Additionally, manufacturing an imaging system with a multitude of bowtie filters increases the overall manufacturing cost of the imaging system.

Therefore, it would be desirable to design an apparatus and method of dynamically filtering the radiation emitted toward the subject during imaging data acquisition with a single filter.

BRIEF DESCRIPTION OF THE INVENTION

The present invention is a directed method and apparatus of dynamically filtering radiation projected toward a subject for data acquisition overcoming the aforementioned drawbacks.

The present invention includes a filtering apparatus for a CT imaging system or equivalently for an x-ray imaging system. The filtering apparatus is designed such that its shape may be changed prior to or during an imaging session. The shape of the filtering apparatus can be modulated to mirror an attenuation pattern of a subject thereby optimizing radiation dose exposure to the subject. Furthermore, by implementing two opposing filters that are orthogonally oriented with respect to one another, the x-ray attenuation may be controlled along the x as well as z axes to shape the x-ray intensity. A number of filtering apparatuses are contemplated.

In accordance with one aspect of the present invention, a method of diagnostic imaging comprises the steps of positioning a subject to be scanned into a scanning bay and projecting a radiation beam along a beam path toward the subject. The method further includes positioning a filter having an attenuation profile in the beam path. The attenuation profile of the filter is then modulated to define a desired attenuation profile. The method further includes acquiring diagnostic data of the subject and reconstructing an image of the subject from the diagnostic data.

In accordance with another aspect of the present invention, a method of acquiring diagnostic data of a subject comprises the steps of determining an attenuation pattern for acquiring diagnostic data of a subject to be scanned and presetting a first filter to a desired attenuation profile. The method further includes the step of projecting high frequency electromagnetic energy toward the subject to acquire diagnostic data of the subject. During the projection of high frequency electromagnetic energy, a second filter having an attenuation profile is translated such that the attenuation profiles of the first filter and the second filter is a function of the attenuation pattern of the subject.

In accordance with a further aspect of the present invention, a method of diagnostic imaging includes the steps of positioning a subject to be scanned on a table in a scanning bay and projecting high frequency electromagnetic energy toward the subject. The method further includes dynamically filtering the high frequency electromagnetic energy with at least one filter and acquiring imaging data of the subject. A set of images of the subject from the imaging data are then reconstructed. With the subject removed from the scanning bay, high frequency electromagnetic energy is again projected toward the detector absent the subject and table and dynamically filtered with the at least one filter. The method further includes acquiring scan data attributable to the at least one filter and generating a set of calibration data attributable to the at least one filter to be used in reconstructing artifact free images of the subject.

In accordance with yet another aspect of the present invention, a radiation emitting system comprises a scanning bay configured to position the subject to be scanned in a path of radiation as well as a radiation projection source configured to project radiation toward the subject. The system further includes a radiation filter having a variable attenuation profile. A computer is also provided and programmed to determine an attenuation pattern of the subject and modulate the variable attenuation profile of the radiation filter as a function of the attenuation pattern of the subject.

In accordance with a further aspect of the present invention, a radiation emitting imaging system is provided. The imaging system includes a scanning bay and a moveable table configured to move a subject to be scanned fore and aft along a first direction within the scanning bay. The system further includes an x-ray projection source configured to project x-rays toward the subject. A first attenuator is provided and configured to attenuate x-rays along a first axis. A second attenuator is also provided and configured to attenuate x-rays along a second axis. Both the first attenuator and second attenuator are translatable in the first direction. The imaging system further includes a computer programmed to calibrate the first attenuator to have a desired attenuation profile and calibrate the second attenuator to have a desired attenuation profile. The computer is further programmed to move the subject along the first direction and simultaneously therewith, translate at least one of the first attenuator and the second attenuator in the first direction.

In accordance with yet another aspect of the present invention, a computer readable storage medium is provided and has stored thereon a computer program representing a set of instructions that when executed by a computer causes the computer to move a subject to be scanned into a scan position. The set of instructions further causes the computer to determine an attenuation pattern of the subject and manipulate an attenuation profile of a filter configured to filter x-rays projected toward a subject. The computer is also instructed to acquire imaging data of the subject and reconstruct at least one image therefrom.

In accordance with another aspect of the present invention, a filtering apparatus to filter radiation projected toward a subject to be scanned is provided. The filtering apparatus includes a body having a plurality of hollow tubes parallelly arranged and configured to receive and discharge attenuating fluid to define an attenuation profile as a function of an attenuation pattern of the subject.

In accordance with a further aspect of the present invention, a filtering apparatus to filter radiation projected toward a subject to be scanned includes a body constructed so as to be capable of having a plurality of attenuating rods. Each of the attenuating rods is placeable in the body such that an attenuation profile as a function of an attenuation pattern of the subject is defined.

In accordance with yet another aspect of the present invention, a filtering apparatus to filter radiation projected toward a subject to be scanned comprises a flexible bladder containing attenuating fluid. The flexible bladder is configured to be manipulated to modulate the attenuating fluid such that an attenuation profile as a function of an attenuation pattern of the subject is defined.

In accordance with yet another aspect of the present invention, a pre-subject filter having variable attenuation for a radiographic imaging system is provided. The filter includes a first end having a first attenuation profile and a second end having a second attenuation profile. The second attenuation profile is larger than the first attenuation profile. The pre-subject filter is contoured to continuously change the attenuation profile from the first end to the second end.

In accordance with a further aspect of the present invention, a CT system includes a rotatable gantry having an opening defining a scanning bay. This system also includes a movable table configured to translate a subject to be scanned along a first axis within the scanning bay. An x-ray projection source configured to project x-rays toward the subject is also provided. The system further includes a pre-subject filter configured to filter x-rays projected toward the subject when the filter has a shaped cross-section that changes shape as a function of z-axis position. The system also includes a computer programmed to determine attenuation pattern of the subject and translate the filter along the first axis with respect to the attenuation pattern of the subject. The computer is then programmed to acquire imaging data of the subject.

In accordance with yet a further aspect of the present invention, a method of diagnostic imaging comprises the steps of positioning a subject to be scanned and to a scanning bay and projecting a radiation beam along a beam path toward the subject. The method also includes positioning a filter having variable attenuation in the beam path and translating a filter in at least one direction to reduce radiation exposure to sensitive anatomical regions of the subject. The method further includes acquiring imaging data of the subject and reconstructing an image of the subject from the imaging data.

In accordance with another aspect of the present invention, a radiographic imaging system is provided and includes a scanning bay with a movable table configured to move a subject to be scanned fore and aft along a first direction within the scanning bay. The imaging system further includes an x-ray projection source configured to project x-rays in an x-ray beam toward the subject. A pair of cam filters formed of attenuating matter is also provided and controlled by a computer programmed to determine a region-of-interest of the subject and position the pair of cam filters to limit x-ray exposure to the patient area outside the region-of-interest.

In accordance with yet another aspect of the present invention, a cam filter assembly for use with a radiation emitting imaging system is provided. The cam filter assembly includes a pair of cam filters wherein the attenuation varies with thickness of the cam filter. The pair of cam filters is also configured to operate in tandem to manipulate a beam of radiation projected toward a subject to limit radiation exposure to the patient area outside the region-of-interest of the subject.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 5 is a perspective view of one embodiment of a dynamic filter in accordance with the present invention.

FIG. 6 is a perspective view of another embodiment of a dynamic filter in accordance with the present invention.

FIG. 7 is a perspective view of another embodiment of a dynamic filter in accordance with the present invention.

DETAILED DESCRIPTION OF THE PREFERRED EMBODIMENT

Figure 1:
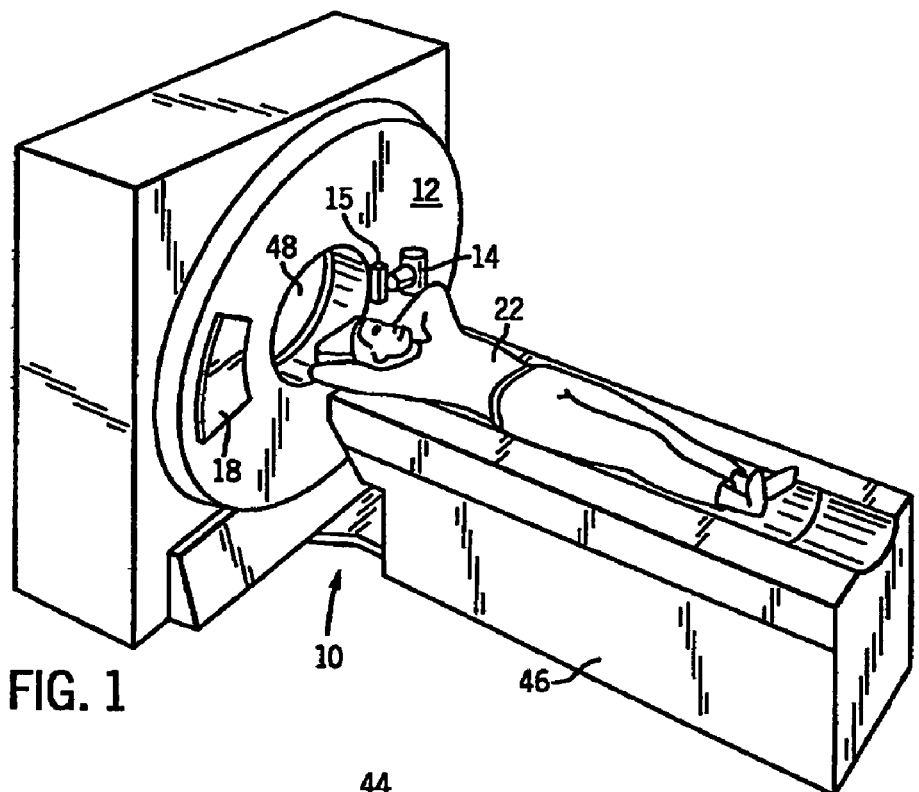
FIG. 1 is a pictorial view of a CT imaging system.
Figure 2:
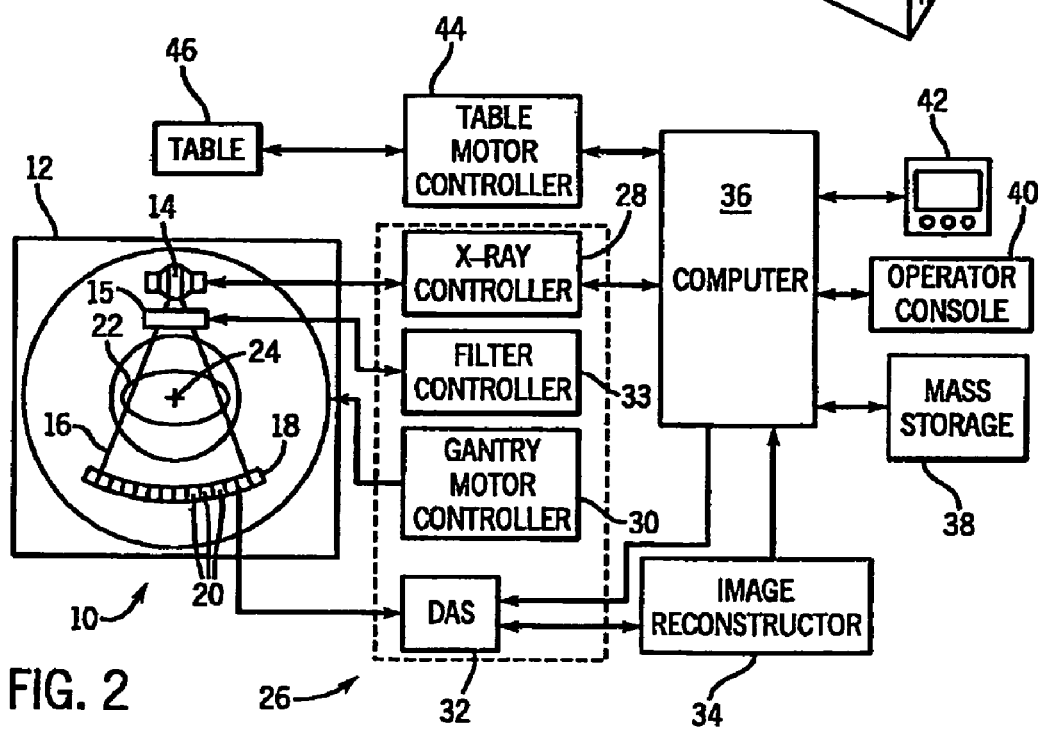
FIG. 2 is a block schematic diagram of the system illustrated in FIG. 1.
Figure 3:
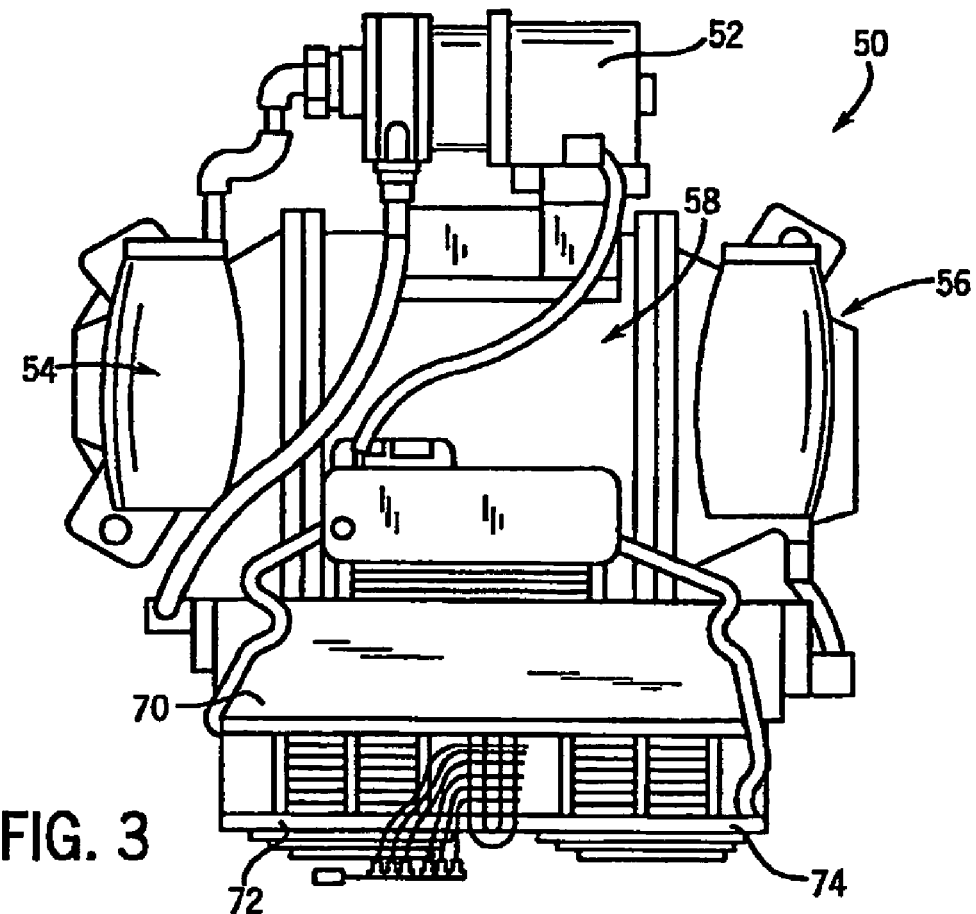
FIG. 3 is a plan view of a representative x-ray system.
Figure 4:
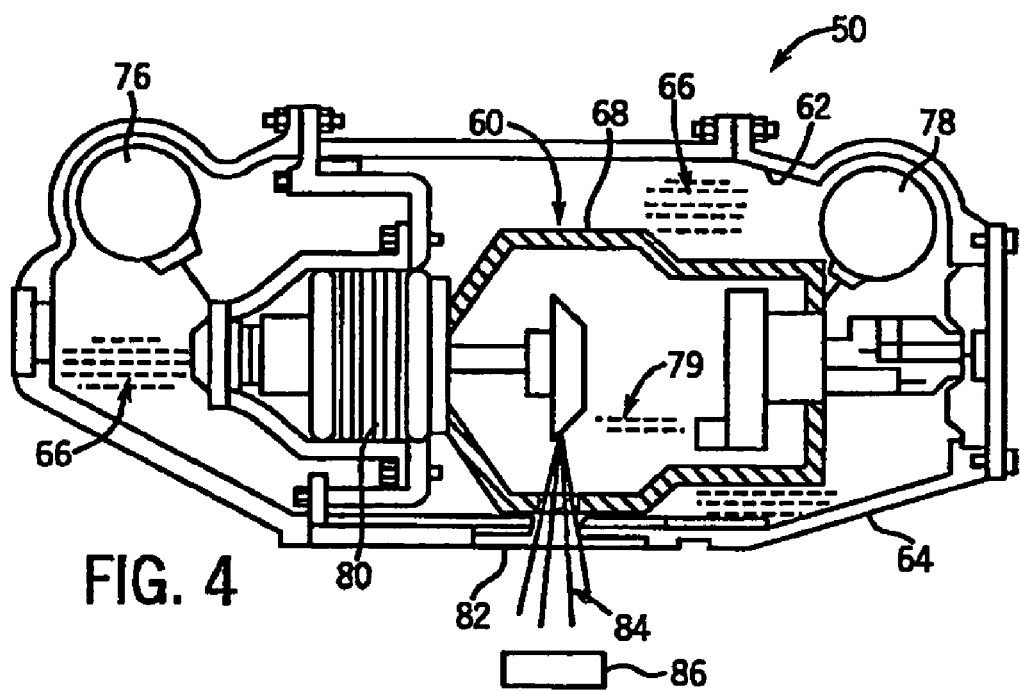
FIG. 4 is a sectional view of a portion of the x-ray system shown in FIG. 1.

The present invention is described with respect to a radiographic imaging system such as the CT system shown in FIGS. 1–2 and the x-ray system shown in FIGS. 3–4. However, it will be appreciated by those skilled in the art that the present invention is equally applicable for use with other radiographic imaging systems. Moreover, the present invention will be described with respect to the emission and detection of x-rays. However, one skilled in the art will further appreciate, that the present invention is equally applicable for the emission and detection of other high frequency electromagnetic energy.

Referring to FIGS. 1 and 2, a "third generation" CT imaging system 10 is shown as including a gantry 12. The present invention, however, is applicable with other CT systems. Gantry 12 has an x-ray source 14 that projects a beam of x-rays 16 through filter 15 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and filter controller 33 that controls filter 15. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Referring now to FIGS. 3–4, an x-ray system 50 incorporating the present invention is shown. The x-ray system 50 includes an oil pump 52, an anode end 54, and a cathode end 56. A central enclosure 58 is provided and positioned between the anode end 54 and the cathode end 56. Housed within the central enclosure 58 is an x-ray generating device or x-ray tube 60. A fluid chamber 62 is provided and housed within a lead lined casing 64. Fluid chamber 62 is typically filled with coolant 66 that will be used to dissipate heat within the x-ray generating device 60. Coolant 66 is typically a dielectric oil, but other coolants including air may be implemented. Oil pump 52 circulates the coolant through the x-ray system 50 to cool the x-ray generating device 60 and to insulate casing 64 from high electrical charges found within vacuum vessel 68. To cool the coolant to proper temperatures, a radiator 70 is provided and positioned at one side of the central enclosure 58. Additionally, fans 72, 74 may be mounted near the radiator 70 to provide cooling air flow over the radiator 70 as the dielectric oil circulates therethrough. Electrical connections are provided in anode receptacle 76 and cathode receptacle 78 that allow electrons 79 to flow through the x-ray system 50.

Casing 64 is typically formed of an aluminum-based material and lined with lead to prevent stray x-ray emissions. A stator 70 is also provided adjacent to vacuum vessel 68 and within the casing 64. A window 82 is provided that allows for x-ray emissions created within the system 50 to exit the system and be projected toward an object, such as, a medical patient for diagnostic imaging. Typically, window 82 is formed in casing 64. Casing 64 is designed such that most generated x-rays 84 are blocked from emission except through window 82.

Referring now to FIGS. 5–9, a number of filter embodiments will be described. It should be noted that each of the embodiments described may be implemented as a pre-patient bowtie filter in a CT imaging system similar to filter 15 shown in FIGS. 1–2 or as a pre-patient filter 86 for an x-ray system similar to that shown in FIGS. 3–4. Specifically, a number of filter embodiments will be described wherein each of the filters may be modulated or "morphed" to define a desired attenuation profile specific to the particular imaging needs of an imaging session. For example, the attenuation profile of the filter may be modulated such that radiation exposure to particular organs is reduced without sacrificing or jeopardizing radiation exposure to other particular regions of interest. As a result, organs or regions of interest either sensitive to radiation exposure or not subject of the imaging session are not unnecessarily subjected to radiation exposure. Additionally, the attenuation profile of the filter may be modulated as a function of viewing angle. For example, the attenuation profile of the filter may be manipulated to filter radiation for a wider region of interest for a top view data acquisition position and likewise be manipulated to have a more narrow profile for a side view data acquisition position. The attenuation profile of the filter may also be modulated as a function of filter position along an imaging axis. For example, the attenuation profile of the filter may be dynamically manipulated during translation of the subject and/or filter to reduce radiation exposure in dose avoidance or reduction regions located between regions of interest. "Dose avoidance" and "dose reduction" refers to certain organs or anatomical regions where reduced radiation exposure is desired during an imaging session. While complete blockage of radiation to these areas is desired, reducing but not eliminating radiation exposure to these regions is acceptable. Therefore, it remains desirable to develop an attenuation profile that reduces if not eliminates radiation exposure to certain anatomical regions of the subject but SNR may be sacrificed with respect to these "avoidance" or "reduction" regions.

Referring now to FIG. 5, one embodiment of the present invention is shown. In this embodiment, filter 100 includes a body 102 defined by a plurality of hollow tubes 104. Hollow tubes 104 are configured to receive attenuating fluid such as a contrast agent. As shown, a selected number of the hollow tubes have been flooded with the attenuating fluid to define an attenuation profile. The attenuation profile defined by the attenuating fluid flooded into the hollow tubes is only one example. That is, any number of the hollow tubes may be filled with attenuating fluid to define a desired attenuation profile. The attenuating fluid is stored in a reservoir (not shown) and a computer or control mechanism floods the tubes to define the desired attenuation profile needed for the imaging session or for a moment in the imaging session. That is, depending upon the needs of the imaging session, the tubes may be filled and flushed dynamically throughout the imaging session to vary the attenuation profile during data acquisition. A number of techniques of removing or flushing attenuating fluid from a tube are contemplated including a computer controlled system of valves (not shown) that apply compressed gas to the chambers. Alternately, a series of honeycombed cavities may be equivalently implemented in place of the hollow tubes.

Referring now to FIG. 6, another embodiment of the filter in accordance with the present invention is shown. In this embodiment, filter 106 includes a body 108 defined by a number of attenuating rods 110. Operation of filter 106 is similar to operation of filter 100 of FIG. 5. With filter 106, each attenuating rod 110 is positioned within the body such that the plurality of attenuating rods as a whole defines the desired attenuation profile. Filter 106 may be used to filter radiation in a couple of ways. First, that portion of the plurality of attenuating rods 110 having attenuating rods removed may be placed in the x-ray beam path or, conversely, the attenuating rods 110 disposed from the rest of the attenuating rods may be slid into the x-ray beam path. A control and/or computer may be programmed to reposition the attenuating rods to define the desired attenuation profile.

Referring now to FIG. 7, another preferred embodiment of a filtering apparatus 112 includes a flexible bladder 114 containing attenuating fluid positioned between an upper plate 116 and a lower plate or base 117. Bladder 114 is sufficiently flexible such that the attenuating fluid contained therein may be modulated or manipulated to define the desired attenuation profile. Bladder 114 may contain attenuating liquid, gelatin, beads, or the like. Upper plate 116 is fabricated from a flexible x-ray transparent material such as plastic that, in response to an applied force, alters the shape of the flexible bladder 114. In one embodiment, the upper plate responds to a force applied by at least one of a number of moveable rods 118. The moveable rods 118 are controlled by a computer to distort the upper plate such that the flexible bladder is likewise distorted. Base plate 118 supports the flexible bladder and is fabricated from a solid x-ray transparent material. Alternatively, base plate 117 could be fabricated to contain x-ray spectral filtration material. It should be noted that flexible bladder 114, upper plate 116, and base plate 117 are each fabricated from an x-ray transparent material so that x-rays are attenuated primarily by the attenuating fluid rather than the bladder or plates.

Figure 8:
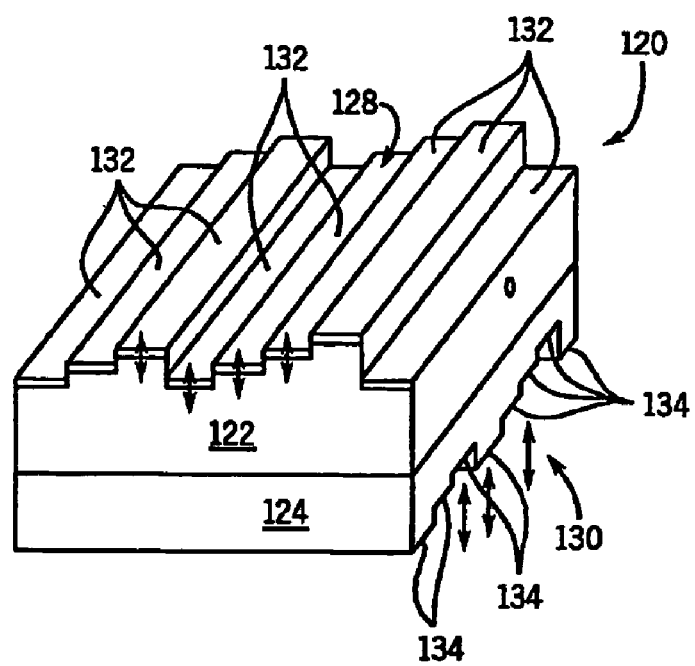
FIG. 8 is a perspective view of another embodiment of a dynamic filter in accordance with the present invention.

Referring now to FIG. 8, another embodiment of a filtering apparatus in accordance with the present invention is shown. In this embodiment, filter 120 includes a first bladder 122 and a second bladder 124. Each bladder 122, 124 is designed to contain attenuating fluid such as attenuating liquid, gelatin, or beads. Filter 120 further includes an intermediary plate 126 disposed between bladder 122 and bladder 124. Filter 120 further includes an upper plate 128 and a lower plate 130. Each plate 128, 130 is formed from a plurality of parallelly aligned slots 132, 134. The slots 132 and 134 of each plate 128 and 130, respectively, impart or release a force applied to bladders 122 and 124. That is, each slot 132 of plate 128 moves perpendicularly with respect to plate 126 to impart a desired force onto bladder 122 such that the attenuating fluid contained within bladder 122 defines a desired attenuation profile. Slots 134 of plate 130 operate in a similar fashion to define a desired attenuation profile for bladder 124. For example, slots 132 may be moved by a computer controlled mechanism such as step actuators to impart a force on bladder 122 to define an attenuation profile along an x axis whereas slots 130 of plate 134 respond to another set of step actuators to define an attenuation profile along a z axis. Collectively, slots 132 and 134 cooperatively define a desired attenuation profile that mirrors a dual-axes attenuation pattern of the subject. The attenuation pattern of the subject may be determined from a scout scan of the subject. Additionally, filter 120 may be implemented with only one of the bladders 122, 124 and only one of the plates 128–130 of slots 132, 134. In this alternate single bladder embodiment, an attenuation profile is defined only along one axis. Moreover, in accordance with another embodiment, the flexible bladders 122, 124 may be manipulated by step actuators (not shown) directly without plates 128 and 130.

Figure 9:
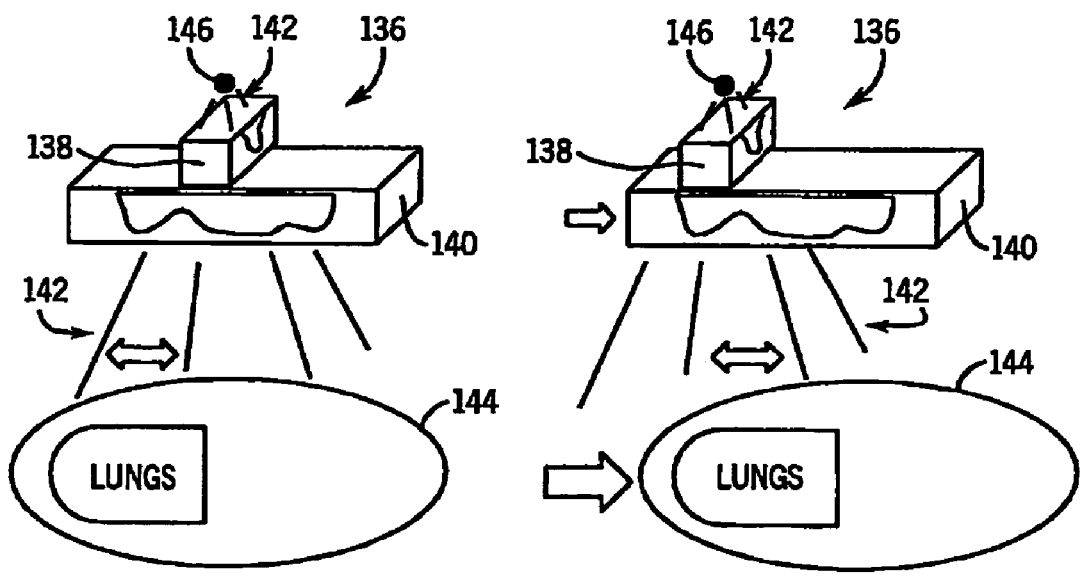
FIG. 9 is a representation of a filtering apparatus during translation in accordance with another aspect of the present invention.

Shown in FIG. 9 is a representation of a filtering apparatus in accordance with another aspect of the present invention during translation in a first direction. In this embodiment, filtering apparatus 136 comprises an x axis filter 138 and a z axis filter 140. Filtering apparatus 136 is designed to filter x-ray beams 142 projected toward a subject 144 by an x-ray source 146. Filters 138 and 140 may comprise any one of the dynamic filters described with respect of FIGS. 5–8. Accordingly, an attenuation profile of filter 138 and an attenuation profile of filter 140 are defined for a moment of x-ray projection. Preferably, the attenuation profiles are defined prior to the imaging session based on the attenuation pattern of the subject 144 determined from a scout scan, but, alternately, the attenuation profiles may be defined during x-ray projection or from a data base of patient demographic information. As shown in FIG. 9, the attenuation profile of filter 138 is set as is the attenuation profile of filter 140. Collectively, attenuation profiles will mirror the attenuation patterns of the subject 144 in both the x and z axis. In operation, as the subject 144 is translated in a first direction by a moveable table filter 138 is synchronously translated in the first direction as well. As a result, the collective attenuation profile of filters 138 and 140 mirror the attenuation pattern of the subject 144 during translation of the patient in the first direction along the z axis. As such, the dosage applied to various anatomical regions of the patient may be optimized to eliminate over exposure of radiation to the patient. While FIG. 9 shows translation of the z axis filter 140, the x axis filter 138 could likewise be translated with patient movement.

Figure 10:
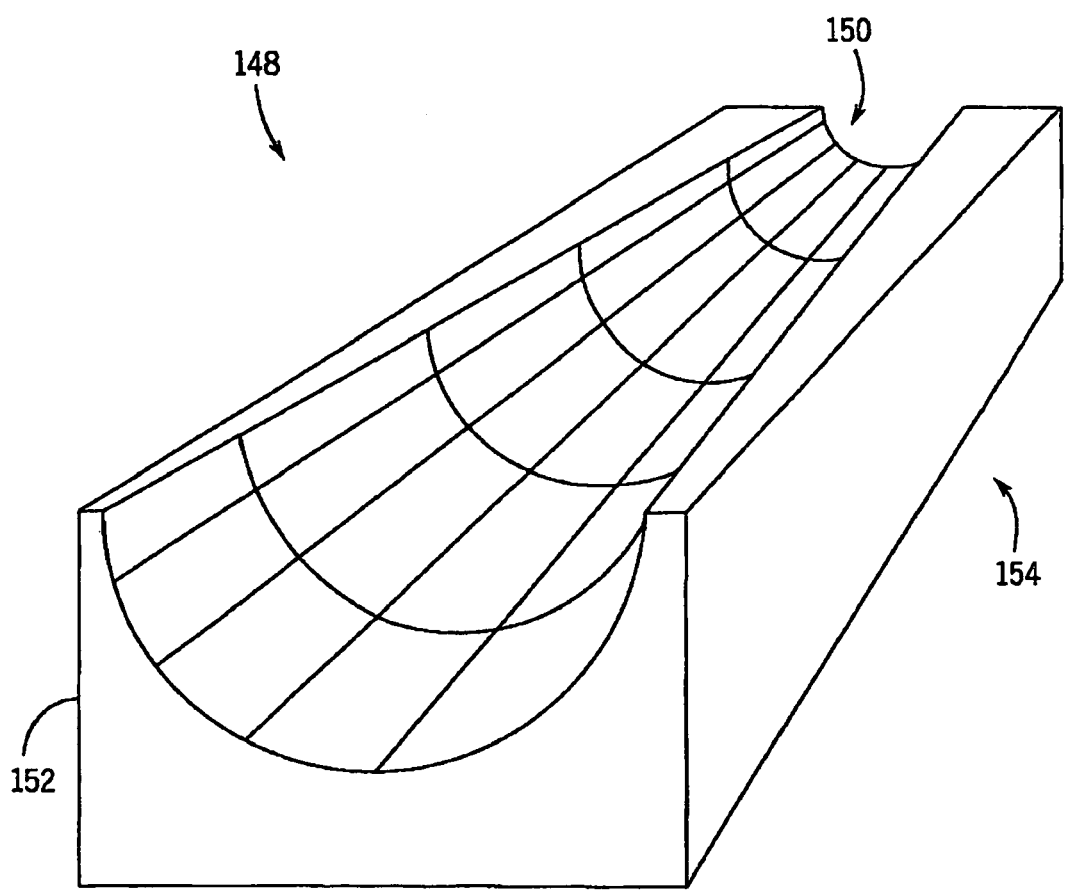
FIG. 10 is a perspective view of another embodiment of a pre-subject filter in accordance with the present invention.

Referring now to FIG. 10, a perspective view of a pre-subject filter in accordance with another aspect of the present invention is shown. In this embodiment, the pre-subject filter 148 includes a first end 150 and a second end 152. A body region 154 is disposed therebetween to connect first end 150 and second end 152 to one another. As shown, filter 148 has a cross-section that narrows from the second end 152 to the first end 150. That is, first end 150 has a filtering region that is narrower than the filtering region of second end 152. Additionally, the attenuation profile of first end 150 is larger than the attenuation profile of second end 152. That is, the filtering material is thicker at the first end 150 than at the second end 152. In the illustrated embodiment, the filtering material thickness changes linearly from the first end 150 to the second end 152.

Filter 148 is designed such that it may be translated in a direction along the z-axis of a radiographic imaging system. That is, filter 148 may be translated such that the attenuation achieved by filter 148 generally complements the attenuation pattern of the subject to be scanned. As a result, anatomical regions or organs sensitive to radiation exposure may be protected against unnecessary radiation exposure. Furthermore, filter 148 is configured to be translated in a transverse direction as well. As a result, filtration with respect to the attenuation pattern of the subject may be achieved. To further reduce radiation exposure to the subject, filter 148 may be repositioned as a function of view angle.

The filter can be easily calibrated prior to patient scanning by collecting and storing data representing the filter attenuation at two or more filter positions. During patient scanning, the appropriate attenuation profile is determined for correction during image reconstruction by interpolation and/or extrapolation.

Figure 11:
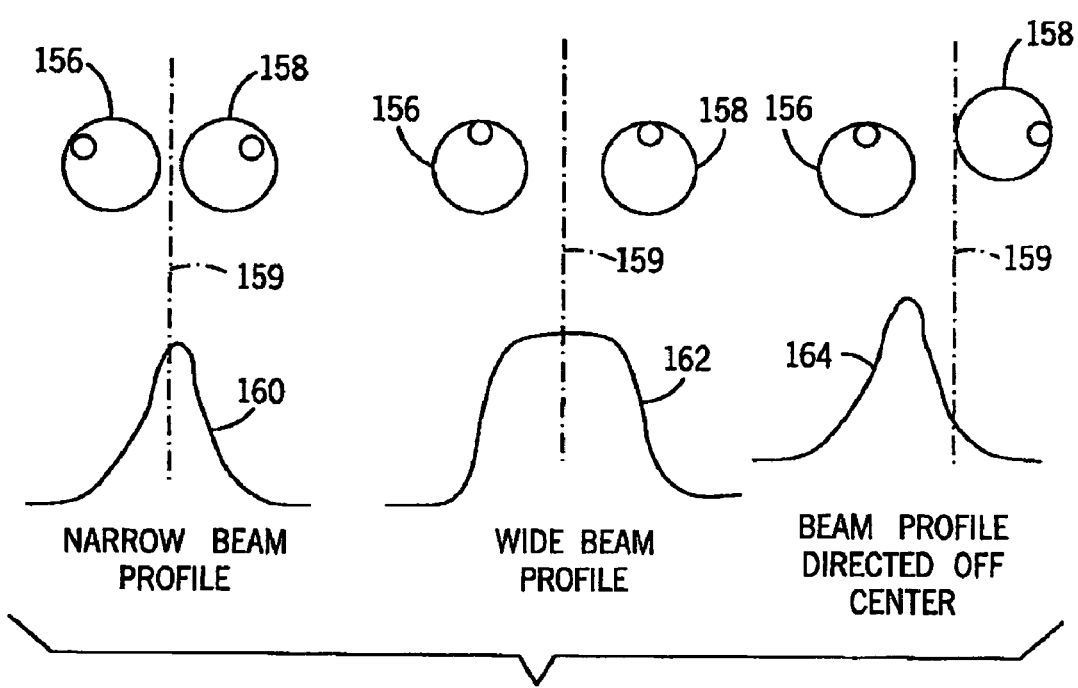
FIG. 11 is a schematic representation of a pair of cam filters configured to operate in tandem to manipulate an x-ray beam projected toward a subject in accordance with the present invention.

Referring now to FIG. 11, a schematic representation of a pair of cam filters configured to operate in tandem to manipulate an x-ray beam projected toward a subject in accordance with the present invention is illustrated. As shown, a pair of cam filters 156, 158 is configured to operate in tandem to manipulate an x-ray beam 159, schematically shown as a dashed line about a vertical axis between the filters, to limit radiation exposure outside the desired region-of-interest (ROI) of a subject. By operating filters 156, 158 in tandem, the profile of an x-ray may be manipulated. For example, the filter 156, 158 may be spaced closer to the beam path 159 to create a narrow beam profile 160 and spaced apart to create a wider beam profile 162. Additionally, one filter 156 may be moved away from the beam 159 and the other filter 158 moved closer to the beam 159 to cause the beam profile to be off-center.

Filters 156, 158 are configured to be oriented along an x-axis of the subject to be scanned and may also be translated along the length of the subject to manipulate the beam profile with respect to the attenuation pattern of the subject to reduce radiation exposure to radiation sensitive or dose reduction regions of the subject. In a further embodiment, the intensity of the x-ray beam along the x-axis may be manipulated by configuring the filters to have a varying attenuation profile. For example, each filter may be configured such that the thickness of the attenuation material varies with the length of the filter. As such, different portions of the filter may be placed in the x-ray beam path to alter the filtering of the x-ray beam. Alternately, the filters could be formed to have a constant thickness but the density of the filtering material varies along the length of the filter. Other embodiments are contemplated including fabricating the filters to have different sections or cores wherein each section has a different filtering power and depending upon the clinical needs of the imaging session, different sections are placed in the beam path. In another embodiment, each filter has an elliptical shape to reduce x-ray intensity drop off rate.

As is indicated previously, a scout scan may be performed of the subject to determine a filter contour that best fits the complement of the patient's attenuation pattern. Accordingly, special needs of the imaging session for the patient such as dose avoidance or reduction regions or regions of increased x-ray necessity may be accounted for in defining the patient's attenuation pattern. Also, as indicated previously, the attenuation profile of filters may be preset prior to the imaging session or dynamically modulated during the imaging session to mirror or complement the attenuation pattern of the subject.

In a further embodiment of the present invention, one or more dynamic filters may be used to filter radiation during the acquisition of imaging data of a subject. A set of images can then be reconstructed according to well known reconstruction techniques of the subject based on the filtered imaging data. However, the imaging data is susceptible to the presence of artifacts and the set of images associated with the one or more filters itself. Accordingly, the patient is removed from the scanning bay and another set of scan data is acquired wherein the one or more filters are dynamically defined as they were during the imaging of the patient. As a result, a set of calibration data is obtained attributable to the one or more dynamically configured filters. Therefore, a set of images of the of the patient can be reconstructed using the calibration data and usual correction methods. The present invention has been described with respect to a number of embodiments of a dynamic filter to be implemented in a radiographic imaging system. The various embodiments may be utilized to dynamically modulate the attenuation profile of the filter prior to and/or during the imaging session to mirror the attenuation pattern of the subject and thereby reduce radiation exposure to the patient.

Accordingly, in accordance with one embodiment of the present invention, a method of diagnostic imaging comprises the steps of positioning a subject to be scanned into a scanning bay and projecting a radiation beam along a beam path toward the subject. The method further includes positioning a filter having an attenuation profile in the beam path. The attenuation profile of the filter is then modulated to define a desired attenuation profile. The method further includes acquiring diagnostic data of the subject and reconstructing an image of the subject from the diagnostic data.

In accordance with another embodiment of the present invention, a method of acquiring diagnostic data of a subject comprises the steps of determining an attenuation pattern for acquiring diagnostic data of a subject to be scanned and presetting a first filter to a desired attenuation profile. The method further includes the step of projecting high frequency electromagnetic energy toward the subject to acquire diagnostic data of the subject. During the projection of high frequency electromagnetic energy, a second filter having an attenuation profile is translated such that the attenuation profiles of the first filter and the second filter is a function of the attenuation pattern of the subject.

In accordance with a further embodiment of the present invention, a method of diagnostic imaging includes the steps of positioning a subject to be scanned on a table in a scanning bay and projecting high frequency electromagnetic energy toward the subject. The method further includes dynamically filtering the high frequency electromagnetic energy with at least one filter and acquiring imaging data of the subject. A set of images of the subject from the imaging data are then reconstructed. With the subject removed from the scanning bay, high frequency electromagnetic energy is again projected toward the detector absent the subject and table and dynamically filtered with the at least one filter. As a result, a set of calibration data is obtained attributable to the one or more dynamically configured filters. Therefore, a set of images of the patient can be reconstructed using the calibration data and usual correction methods.

In accordance with yet another embodiment of the present invention, a radiation emitting system comprises a scanning bay configured to position the subject to be scanned in a path of radiation as well as a radiation projection source configured to project radiation toward the subject. The system further includes a radiation filter having a variable attenuation profile. A computer is also provided and programmed to determine an attenuation pattern of the subject and modulate the variable attenuation profile of the radiation filter as a function of the attenuation pattern of the subject.

In accordance with a further embodiment of the present invention, a radiation emitting imaging system is provided. The imaging system includes a scanning bay and a moveable table configured to move a subject to be scanned fore and aft along a first direction within the scanning bay. The system further includes an x-ray projection source configured to project x-rays toward the subject. A first attenuator is provided and configured to attenuate x-rays along a first axis. A second attenuator is also provided and configured to attenuate x-rays along a second axis. Both the first attenuator and second attenuator are translatable in the first direction. The imaging system further includes a computer programmed to calibrate the first attenuator to have a desired attenuation profile and calibrate the second attenuator to have a desired attenuation profile. The computer is further programmed to move the subject along the first direction and simultaneously therewith, translate at least one of the first attenuator and the second attenuator in the first direction.

In accordance with yet another embodiment of the present invention, a computer readable storage medium is provided and has stored thereon a computer program representing a set of instructions that when executed by a computer causes the computer to move a subject to be scanned into a scan position. The set of instructions further causes the computer to determine an attenuation pattern of the subject and manipulate an attenuation profile of a filter configured to filter x-rays projected toward a subject. The computer is also instructed to acquire imaging data of the subject and reconstruct at least one image therefrom.

In accordance with another embodiment of the present invention, a filtering apparatus to filter radiation projected toward a subject to be scanned is provided. The filtering apparatus includes a body having a plurality of hollow tubes parallelly arranged and configured to receive and discharge attenuating fluid to define an attenuation profile as a function of an attenuation pattern of the subject.

In accordance with a further embodiment of the present invention, a filtering apparatus to filter radiation projected toward a subject to be scanned includes a body constructed to be capable of having a plurality of attenuating rods. Each of the attenuating rods is placeable in the body such that an attenuation profile as function of an attenuation pattern of the subject is defined.

In accordance with yet another embodiment of the present invention, a filtering apparatus to filter radiation projected toward a subject to be scanned comprises a flexible bladder containing attenuating fluid. The flexible bladder is configured to be manipulated to modulate the attenuating fluid such that an attenuation profile as a function of an attenuation pattern of the subject is defined.

In accordance with yet another embodiment of the present invention, a pre-subject filter having variable attenuation for a radiographic imaging system is provided. The filter includes a first end having a first attenuation profile and a second end having a second attenuation profile. The second attenuation profile is larger than the first attenuation profile. The pre-subject filter continuously varies the attenuation profile in the z-axis between the first end and the second end.

In accordance with a further embodiment of the present invention, a CT system includes a rotatable gantry having an opening defining a scanning bay. This system also includes a movable table configured to translate a subject to be scanned along a first axis within the scanning bay. An x-ray projection source and configured to project x-rays toward the subject. The system further includes a pre-subject filter configured to filter x-rays projected toward the subject. The system also includes a computer programmed to determine attenuation pattern of the subject and translate the filter along the first axis with respect to the attenuation pattern of the subject. The computer is then programmed to acquire imaging data of the subject.

In accordance with yet a further embodiment of the present invention, a method of diagnostic imaging comprises the steps of positioning a subject to be scanned and to a scanning bay and projecting a radiation beam along a beam path toward the subject. The method also includes positioning a filter having variable attenuation in the beam path and translating a filter in at least one direction to reduce radiation exposure to sensitive anatomical regions of the subject. The method further includes acquiring imaging data of the subject and reconstructing an image of the subject from the imaging data.

In accordance with another embodiment of the present invention, a radiographic imaging system is provided and includes a scanning bay with a movable table configured to move a subject to be scanned fore and aft along a first direction within the scanning bay. The imaging system further includes an x-ray projection source configured to project x-rays in an x-ray beam toward the subject. A pair of cam filters formed of attenuating matter is also provided and controlled by a computer programmed to determine a region-of-interest of the subject and position the pair of cam filters to limit x-ray exposure to the patient area outside the region-of-interest.

In accordance with yet another embodiment of the present invention, a cam filter assembly for use with a radiation emitting imaging system is provided. The cam filter assembly includes a pair of cam filters wherein each cam filter has an attenuation power that varies with thickness of the filter. The pair of cam filters is also configured to operate in tandem to manipulate a beam of radiation projected toward a subject to limit radiation exposure to a region-of-interest of the subject.

The present invention has been described in terms of the preferred embodiment, and it is recognized that equivalents, alternatives, and modifications, aside from those expressly stated, are possible and within the scope of the appending claims.

What is claimed is:

1. A radiographic imaging system comprising:
    a scanning bay;
        a movable table configured to move a subject to be scanned fore and aft along a first direction within the scanning bay;
        an x-ray projection source configured to project x-rays in an x-ray beam toward the subject;
        a pair of generally cylindrically-shaped rotatable filters formed of attenuating matter, each filter rotatable about a line of rotation that extends along a long axis of the filter and is defined to be transverse to the x-ray beam; and
        a computer programmed to:
            determine a region-of-interest of the subject; and rotate at least one rotatable filter of the pair of rotatable filters such that the pair of rotatable filters limit x-ray exposure outside the region-of-interest.

2. The radiographic imaging system of claim 1 wherein each cam filter has a length and an attenuation profile that varies as a function of filter length.

3. The radiographic imaging system of claim 1 wherein an attenuation profile of each filter is a function of filter thickness.

4. A cam filter assembly for use with a radiation emitting imaging system, the cam filter assembly including a pair of non-overlapping cam filters wherein each cam filter has a generally rod-shaped body and has an attenuation power that varies with thickness of the filter, the pair of cam filters being configured to be independently rotated to collectively manipulate a beam of radiation projected toward a subject to generate a desired radiation profile across a region-of-interest of the subject.

5. The cam filter assembly of claim 4 wherein each filter has a width situated along an x-axis and a length situated along a z-axis, the z-axis being parallel to a long axis of the subject, and wherein each filter has varying attenuation characteristics along its length.

* * * * *